US 7,075,058 B2

(12) United States Patent
Chinn et al.

(10) Patent No.: US 7,075,058 B2
(45) Date of Patent: Jul. 11, 2006

(54) PHOTOTHERMAL IMAGING SCANNING MICROSCOPY

(75) Inventors: Diane Chinn, Pleasanton, CA (US); Christopher J. Stolz, Lathrop, CA (US); Zhouling Wu, Pleasanton, CA (US); Robert Huber, Discovery Bay, CA (US); Carolyn Weinzapfel, Tracy, CA (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 331 days.

(21) Appl. No.: 10/402,604

(22) Filed: Mar. 28, 2003

(65) Prior Publication Data

US 2004/0188602 A1   Sep. 30, 2004

(51) Int. Cl.
*G01N 21/41* (2006.01)

(52) U.S. Cl. ...................... 250/234; 356/432
(58) Field of Classification Search ........ 250/234–236, 250/341.1, 341.2, 341.6, 338; 356/432, 433; 374/5, 57; 430/330

See application file for complete search history.

(56) References Cited

U.S. PATENT DOCUMENTS

| 4,521,118 | A |   | 6/1985  | Rosencwaig |        |
|-----------|---|---|---------|------------|--------|
| 4,634,290 | A | * | 1/1987  | Rosencwaig et al. | 374/5 |
| 4,854,710 | A | * | 8/1989  | Opsal et al. | 356/432 |
| 5,074,669 | A | * | 12/1991 | Opsal | 356/445 |
| 5,574,562 | A | * | 11/1996 | Fishman et al. | 356/432 |
| 6,081,127 | A | * | 6/2000  | Wagner et al. | 324/765 |

OTHER PUBLICATIONS

Chow, R., et al., "Absorptance behavior of optical coatings for high-average-power laser applications," Applied Optics, vol. 39, No. 4, Feb. 1, 2000, pp. 650-658.
Chow, R., et al., "Absorptance Measurements of Transmissive Optical Components by the Surface Thermal Lensing Technique," LLNL, UCRL-JC-128008, Sep. 24, 1997, 11 pages.
Wu, Z, et al., "Damage threshold prediction of hafnia-silica multiplayer coatings by nondestructive evaluation of fluence-limiting defects," Applied Optics, vol. 40, No. 12, Apr. 20, 2001, pp. 1897-1906.
Wu, Z., et al., "Non-destructive evaluation of thin film coatings using a laser-induced surface thermal lensing effect," Elsevier Science S.A., Thin Solid Films 290-291 (1996) pp. 271-277.

(Continued)

*Primary Examiner*—Stephone B. Allen (57) ABSTRACT

Photothermal Imaging Scanning Microscopy produces a rapid, thermal-based, non-destructive characterization apparatus. Also, a photothermal characterization method of surface and subsurface features includes micron and nanoscale spatial resolution of meter-sized optical materials.

30 Claims, 3 Drawing Sheets

OTHER PUBLICATIONS

Wu, Z., et al., "Overview of photothermal characterization of optical thin film coatings," SPIE, vol. 2714, pp. 465-479.

Jackson, W.B., et al., "Photothermal deflection spectroscopy and detection," Applied Optics, vol. 20, No. 8, Apr. 15, 1981, pp. 1333-1344.

Boyer, D., et al., "Photothermal Imaging of Nanometer-Sized Metal Particles Among Scatterers," Science, vol. 297, Aug. 16, 2002, pp. 1160-1163.

Han, Y., et al., "Pulsed photothermal deflection and diffraction effects: numerical modeling based on Fresnel diffraction theory," Opt. Eng., 38(12) (Dec. 1999) pp. 2122-2128.

* cited by examiner

PHOTOTHERMAL IMAGING SCANNING MICROSCOPY

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates to a photothermal non-destructive evaluation system and method for investigating surface and subsurface features on optical materials. More specifically, the present invention provides a Photothermal Imaging Scanning Microscopy (PISM) system and method capable of investigating full-size optics of up to a meter in diameter in manageable time frames and additionally capable of nanoscale-resolution images by investigating areas of interest.

2. State of Technology

Optical loss in materials plays an important role in high-power laser applications. Losses in optical components often limit the output of high-power laser systems. The losses in dielectric thin films, particularly due to absorption, are usually higher than in bulk optical materials and depend largely on the thin film deposition method used. Therefore, to develop high-quality optical thin films, it is essential that losses be accurately characterized. A number of thermal imaging techniques have presently been applied to characterization of optical materials and in particular to optical coatings. Photothermal Microscopy (PTM), as one such imaging technique, is a tool for non-destructive evaluation of surface and subsurface structures. By measuring localized optical absorption at discrete laser wavelengths, PTM can map optical absorption, scattering and reflectivity, as well as thermal absorption in materials. However, large-area scanning of optical components with such a technique is limited by extremely slow imaging times. For example, imaging a 1 square cm area of a thin film coating having a 10-micron resolution takes about 278 hours. Such a scan time makes PTM non-feasible for full aperture inspection of large-size (e.g., up to about 1 meter) optics.

Background information on a variety of other thermal techniques, including photothermal deformation (e.g., deflection), thermal lensing, and photothermal microscopy (PTM), is contained in "*Overview of photothermal characterization of optical thin film coatings*," by Z. L. Wu and M. Thompsen, *SPIE*, Vol. 2714, (1996), pp. 465–479, including the following: "[o]ne of the most sensitive detection methods for thermal waves is the photothermal deformation technique . . . . This detection technique uses a modulated (periodically modulated or pulsed) laser beam, referred to as the pump beam or heating beam, to generate thermal waves. The detection of the thermal waves is accomplished by using a second laser beam, referred to as the probe beam, which is reflected from the sample surface. The probe beam monitors the slope of the deformation caused by the thermal expansion effect . . . the technique has the ability to characterize local optical and thermal properties, which are of great importance to the study of thin films for high power laser applications."

Additional background information on PTM and specifically, on using the thermal lensing effect to study thin film coatings is contained in "Non-destructive evaluation of thin film coatings using a laser-induced surface thermal tensing effect," by Z. L. Wu et. al., *Thin Solid Films*, 290–291 (1996) 271–277 including the following: "[w]e report a different technique for studying surface deformation by using an optical diffraction effect. In this detection scheme, the laser-induced thermal-bump behaves as a curved mirror which can either focus or defocus a second probe laser bean through optical diffraction, depending on the specific geometry used."

Accordingly, the present invention provides a quality control non-destructive surface and sub-surface characterization apparatus and method for rapidly scanning large-scale optical components.

SUMMARY OF THE INVENTION

Accordingly, the present invention provides a thermal-based non-destructive scanning imaging apparatus, equipped with an array detector and x,y,z translation stage technology that is capable of producing a constructed photothermal image from one or more predetermined areas of a substantially large-aperture material.

Another aspect of the present invention provides a nanoscale thermal-based scanning imaging apparatus that includes an array detector and x,y,z translation stage technology, capable of imaging specific nanometer-sized areas of interest on a sample.

A further aspect of the present invention is to provide a method of optically pumping a localized area on a sample with a first laser beam to produce a periodically heat-deformed area, then probing the heat-deformed area with a second laser beam, next collecting the radiation from the second laser beam with an array detector, and finally scanning the sample to investigate one or more predetermined areas on the material, wherein a constructed photothermal image from the one or more predetermined areas of a substantially large surface area material is capable of being produced from the collected radiation.

Accordingly, the present invention provides a quality control non-destructive surface and sub-surface characterization apparatus and method for rapidly scanning large-scale optical components. Such a thermal scanning and imaging optical tool is capable of identifying defects and potential laser damage sites in small-aperture (i.e., less than about 5 cm) and large-aperture (i.e., up to about a meter) optics. Moreover, the present invention provides an inspection tool with applications ranging from quality assurance, crack detection, corrosion detection, and bonding properties of various materials.

BRIEF DESCRIPTION OF THE DRAWINGS

The accompanying drawings, which are incorporated into and form a part of the disclosure, illustrate an embodiment of the invention and, together with the description, serve to explain the principles of the invention.

DETAILED DESCRIPTION OF THE INVENTION

Referring now to the following detailed information, and to incorporated materials; a detailed description of the invention, including specific embodiments, is presented. The detailed description serves to explain the principles of the invention.

Unless otherwise indicated, all numbers expressing quantities of ingredients, constituents, reaction conditions and so forth used in the specification and claims are to be understood as being modified in all instances by the term "about," Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

General Description

The present invention provides a photothermal imaging scanning microscopy (PISM) apparatus and method capable of rapid (i.e., less than about 8 hours), non-destructive characterization of surface and subsurface features of optical components up to a meter in diameter and additionally capable of higher resolution analysis to inspect areas of interest. Generally, a pump source, such as a laser beam, heats the test area while one or more probe beams, e.g., optical laser beams, are arranged to measure optically induced properties, such as, diffraction of light resulting from surface deformation as the heat produced by the pump source is absorbed.

Specific Description

Thermal waves are generated by periodically heating a surface of a sample material. One such method to periodically heat a sample is to intensity modulate a beam of electromagnetic radiation. The present invention utilizes lasers having a wavelength range between about 300 nm and about 1 µm as an electromagnetic source. However, other forms of electromagnetic radiation capable of producing thermal waves can be employed within the design parameters of the present invention, such as, but not limited to, microwaves, radio frequencies, X-rays, gamma rays, beams of electrons, protons, neutrons, ions or molecules and/or passing a modulated electric current through the material.

The pump laser in the present invention is capable of being modulated in a near-field scanning arrangement to address high-resolution images of down to about 50 nm. In addition, the present invention is capable of examining one or more predetermined localized areas of a material with a resolution of down to about 10 µm to enable rapid scan times of about 2 seconds per square area. Such scan times provides unexpectedly superior results in scanning and imaging time frames of less than about 8 hours of the surface area of large-aperture optics of up to a meter in diameter (i.e., 0.785 $m^2$ of area). The various materials capable of being investigated with the present invention include, but is not limited to, fused silica, borosilicate glasses, phosphate glasses, crystalline materials such as KDP, DKDP, etc., and dielectric thin film coatings. Dielectric single or multilayer thin films, in particular, such as, for example, $MgF_2$, $HfO_2$, $SiO_2$, $Ta_2O_{4-5}$, $ZrO_2$, $TiO_2$, $Sc_2O_3$, $Al_2O_3$ etc., often contain defects and/or thermal inhomogeneities due to the thin film deposition method and often limit the output of high-power laser systems. The losses in such coatings are primarily due to absorption and are usually higher than in bulk optical materials.

The present invention is capable of non-destructive evaluation of such defects by measuring the localized optical absorption. By incorporating CCD array technology and computer-controlled large-area x,y,z translation stages capable of handling meter-sized optics, an image from an example detector of the present invention can increase the speed over conventional photothermal microscopy methods by greater than about 5 orders of magnitude. After imaging one or more predetermined areas up to the full surface area of a sample, the present invention is also capable of specific higher resolution inspection of any of the lower resolution predetermined imaged areas by utilizing a nanoscale microscopy imaging embodiment to evaluate any sites deemed of interest to an operator.

Figure 1:
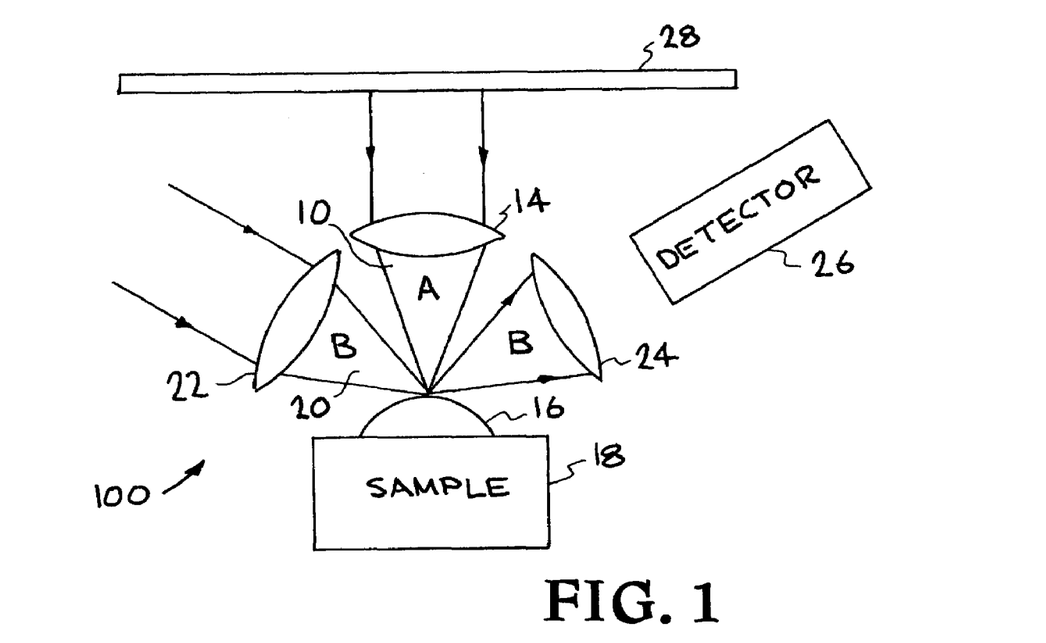
FIG. 1 shows a conventional photothermal microscopy system.

FIG. 1 shows one embodiment of a conventional photothermal microscopy system and is generally designated by the reference numeral 100. System 100 includes, a pump source A, set at a specific wavelength that is typically focused by one or more optical elements 14. Surface and subsurface defects that absorb the light at that specific wavelength induce a thermal bump 16 to form on the surface of a sample substrate material 18. A probe source B is capable of being configured to overlap pump source A at thermally induced bump 16 by a second example optical element 22 and can by optically relayed by a third optical element 24 to detect the change in sample substrate material's 18 surface. A detector 26 can then record changes in probe source's B optical diffraction caused by thermally-induced bump 16. Pump source A is chopped or interrupted periodically by, for example, a chopper wheel 28. Detector 26, such as for example a PIN or a quad photodetector, is electronically locked, by conventional methods and electronics, onto the chopping frequency produced by chopper wheel 28, and a resulting photothermal signal is an indicator of how much heat at a specific wavelength is absorbed. In such a conventional arrangement, pump source A and probe source B are raster-scanned while data is collected a single pixel at a time by detector 26. The conventional raster scanning technique of both pump source A and probe source B can thus generate a photothermal microscopic map of a given rate at about 1 second per pixel, a speed that is impractical for inspecting meter-sized surfaces of materials, e.g., coatings.

Figure 2:
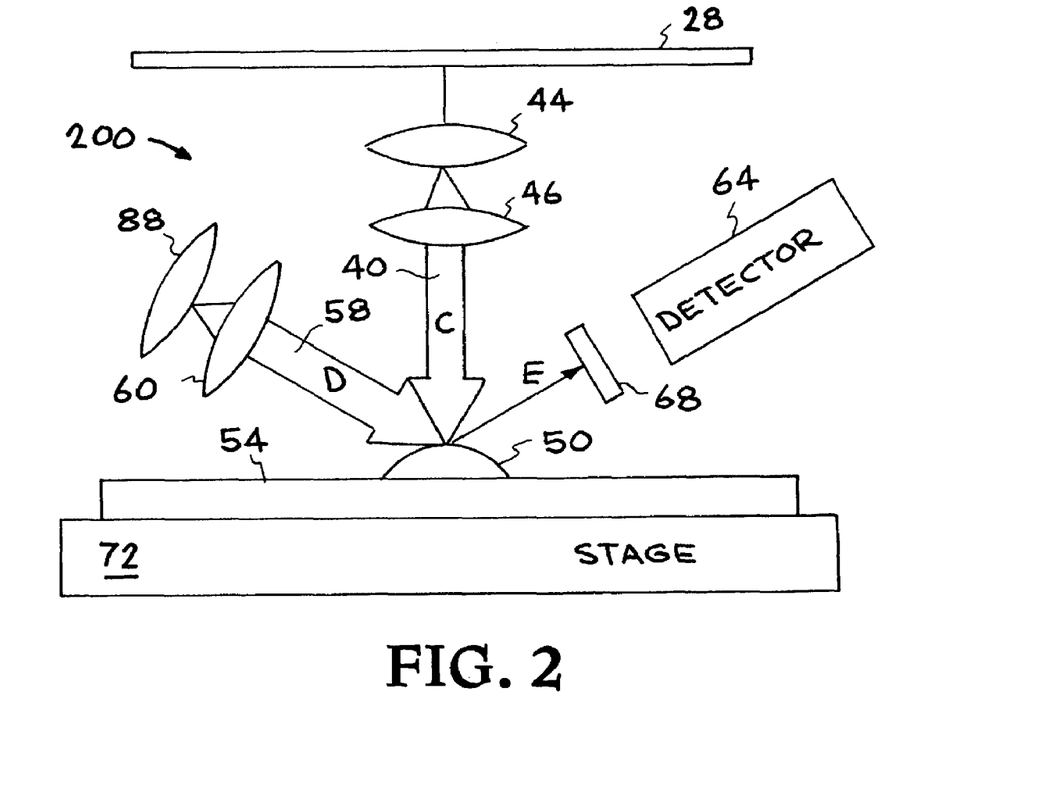
FIG. 2 illustrates a fundamental PSIM embodiment of the present invention.

FIG. 2 illustrates the present invention in its most fundamental embodiment and is generally designated as reference numeral 200. System 200 is capable of arrangement in a dark-field mode (to detect indirect scattered radiation) but more often is arranged in a bright-field-mode where direct scattered radiation is collected and recorded by a detector. The system of the present invention includes a periodically interrupted (i.e., modulated by, for example, chopper wheel 28) electromagnetic pump source C, such as, for example, a CW or pulsed laser beam, that is set at a specific wavelength between about 300 nm and about 1 μm, capable of arrangement to a predetermined spot size between about 2 μm and about 5 mm by, for example, a first pair of optical elements 44, 46. Similar to the system as shown in FIG. 1, surface and subsurface defects (not shown) absorb the light at pump source C wavelength(s) and because of the modulation imposed on pump source C, induce a periodic thermal bump 50 to form on the surface of a sample substrate material 54. One or more probe sources D, such as, a CW laser having a wavelength between about 300 nm and about 1 μm, is capable of being configured to substantially overlap pump source C at bump 50, by, for example, a second pair of optical elements 58 and 60. As a result of the thermally created bump 50, probe source D becomes diffracted to produce a diffracted probe source E, and is recorded as an image, having a resolution of at least 10 μm, of the absorbing defect or inhomogeneity (not shown) by a detector 64 after passing through one or more optical elements 68, such as, for example, optical band-pass filters and/or polarizers. Detector 64 includes mega pixel CCD arrays, such as, for example, a 256×256 array, a 1280×1024 array, more often a 1024×1024, capable of being adapted as a liquid-nitrogen cooled CCD array, an avalanche CCD photodetector, and/or a conventional CCD camera. However, any array CCD capable of meeting the design constraints of the present invention can also be employed. Post processing recorded radiation by detector 64, as detailed hereinafter, and translation with computer controlled x,y,z stages 72, capable of computer-controlled x,y,z translation of a material 54 having diameters of up to about a meter in size allows an entire surface area of such a material 54, e.g., 0.785 m² of area, to be imaged by the present invention in less than about 8 hours.

The present invention utilizes an imaging lock-in technique and operatively coupled electronics to post process the images after collection of the radiation by detector 64. By modulating pump source C and probe source D with a same modulation frequency but varying phase delay, both in-phase and quadrature lock-in images can be computed in post-processing.

Figures 3A, 3B:
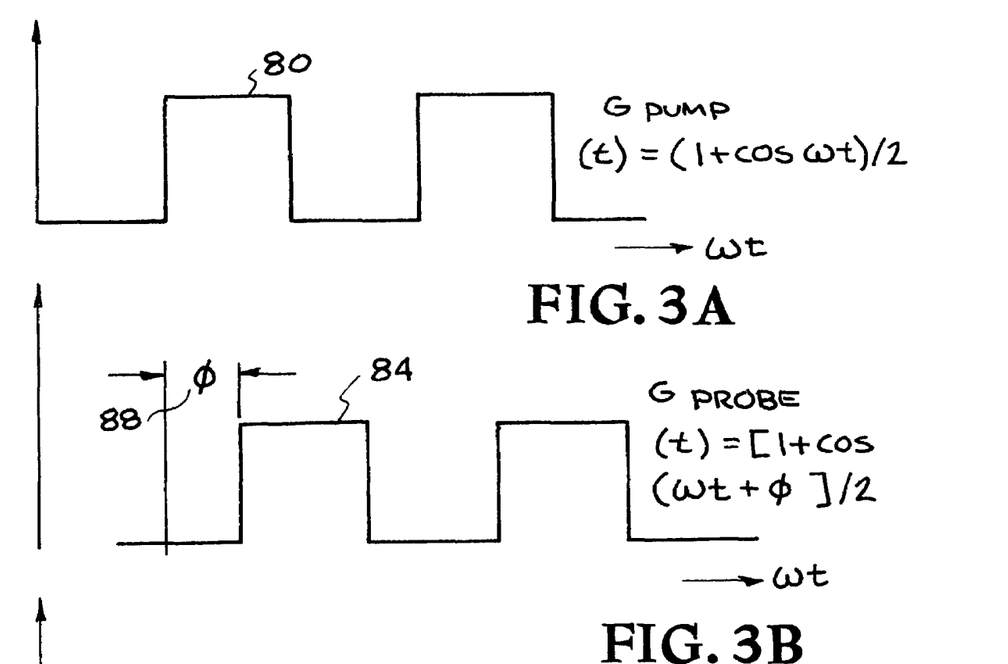
FIG. 3A shows an example pump waveform.
FIG. 3B a shows an example probe waveform.
Figure 3C:
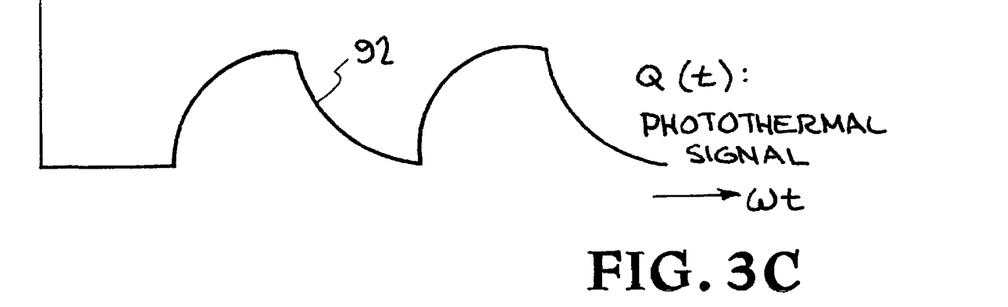
FIG. 3C shows an example of a resultant thermally-induced waveform.

FIG. 3A–C illustrates the optical lock-in concept that includes a pump source waveform 80, as shown in FIG. 3A, a probe source waveform 84, as shown in FIG. 3B, and a resultant photothermal signal waveform 92, as shown in FIG. 3C, each plotted as a respective radian measure (ωt) of phase relationship. Pump waveform 80, as shown in FIG. 3A, is an electronically-produced output signal in synchronization with a frequency modulation imposed on pump source C, as shown in FIG. 2, by, for example, chopper wheel 70, also shown in FIG. 2. Such a modulation (i.e., a periodic interruption of a pump source) causes a photothermal signal 92, as shown in FIG. 3C, to increase and decay with an in-phase relationship with respect to pump waveform 80 as shown in FIG. 3A. Pump waveform 80, is a function that can be computed from the following equation:

$$G_{pump}(t) = (1+\cos \omega t)/2$$

where $\omega = 2\pi f$ radians/sec, f is the frequency in hertz, t=time, and $\omega$ is called the radian frequency of the waveform.

Example probe source waveform 84, as shown in FIG. 3B, is also an electronically produced output signal in synchronization with an apparatus, such as, but not limited to, a chopper wheel or an electro-optical shutter, e.g., a pockels cell, arranged to periodically interrupt, i.e., modulate, probe source D, as shown in FIG. 2, at a same modulation frequency rate as pump source waveform 80, as shown in FIG. 3A. Probe source waveform 84, in synchronization with the modulation frequency imposed upon probe source D, as shown in FIG. 2, is capable of being electronically timed to produce a phase delay 88, with respect to pump waveform 80, as shown in FIG. 3a. Probe source waveform 84, can be computed from the following equation:

$$G_{probe}(t) = [1+\cos(\omega t+\phi)]/2,$$

where $\omega t+\phi$ represents the phase shift of probe source waveform 84, that is induced upon probe source D, and thus diffracted source E, as shown in FIG. 2.

Therefore, images are capable of being recorded by detector 64, as shown in FIG. 2, at electronically timed in-phase and quadrature intervals. Specifically, detector 64, as shown in FIG. 2, is electronically triggered to record images at predetermined optical lock-in phase relationships between pump source C and diffracted probe source E, i.e., at the 0 and 180 in-phase and 90 and 270 quadrature degrees out-of-phase relationships, and such recorded images are post-processed by operatively coupled electronics for image synthesis of a predetermined site, with an amplitude $Q_{(amplitude)}$ and a phase $Q_{(phase)}$ of the recorded signals computed by the following two equations:

$$Q_{(amplitude)} = [(Q_0-Q_{180})^2 + (Q_{90}-Q_{270})^2]^{1/2},$$

$$Q_{(phase)} = \tan^{-1}[(Q_{90}-Q_{270})/(Q_0-Q_{180})],$$

where $Q_0$ and $Q_{180}$ are the 0 and 180 degrees in phase recorded signals and $Q_{90}$ and $Q_{270}$ are the 90 and 270 degrees quadrature recorded signals, respectively.

Figure 4A:
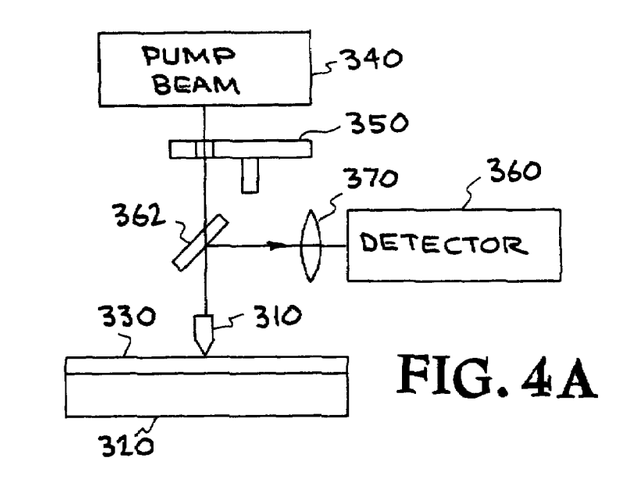
FIG. 4A illustrates a reflection mode PSIM embodiment.
Figure 4B:
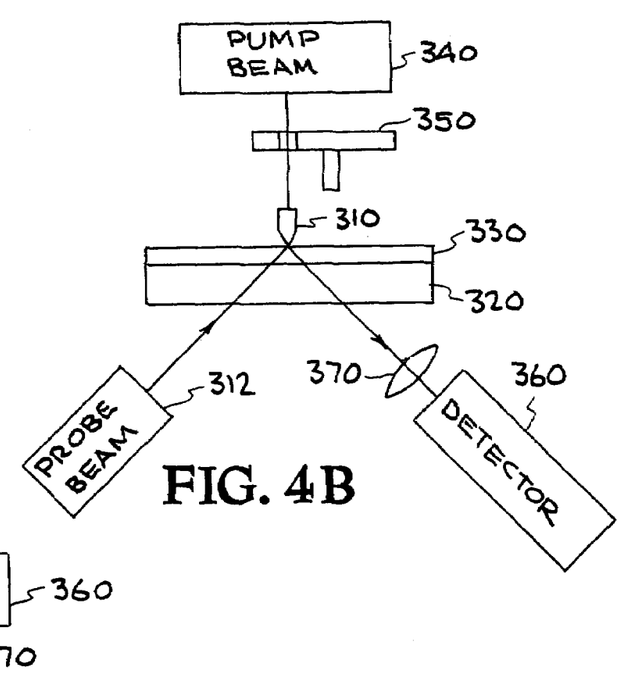
FIG. 4B illustrates an illumination mode PSIM embodiment.
Figure 4C:
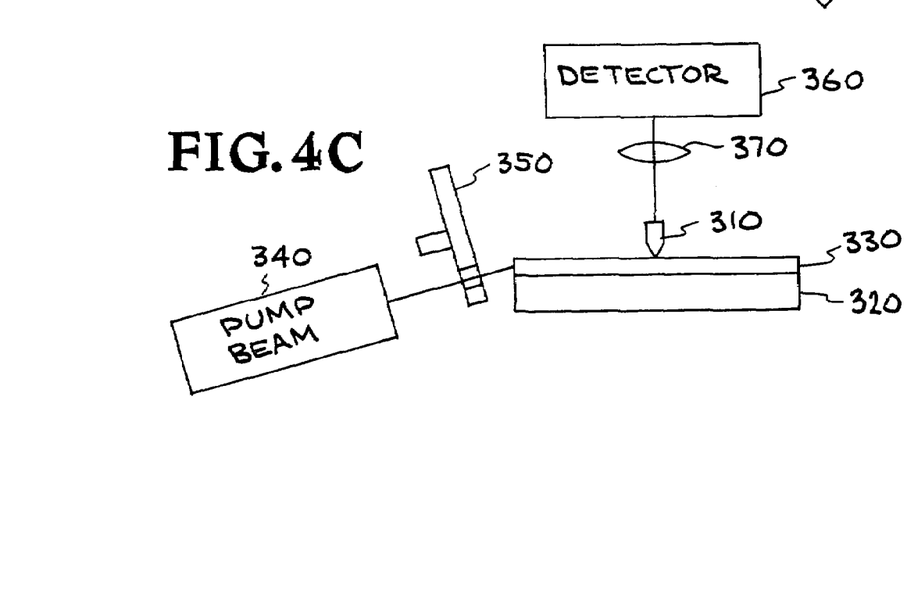
FIG. 4C illustrates a frustrated total internal reflection mode PSIM embodiment.

FIG. 4A–C illustrates high-resolution PSIM embodiments of the present invention utilizing near-field optical microscopy techniques. Near-field optical microscopy is based upon the detection of non-propagating evanescent waves in the near-field region. The near-field region is defined as the region away from the sample that is less than a wavelength of incident light. In near-field scanning optical microscopy (NSOM), this distance is typically on the order of down to about a nanometer. In order to achieve an optical resolution better than the diffraction limit, a probe is brought within the near-field region. The probe in the present invention is capable of detecting in the near-field directly, by means of a sub-wavelength size aperture, or by using the probe as a wave guide with a sub-wavelength scattering source and detecting the evanescent waves as they propagate into the far-field.

One of the difficulties in near-field scanning optical microscopy is keeping the tip at about a constant height above the sample. This is necessary because of the exponential decay of the evanescent waves. If the near field probe source is not kept at a constant height above a sample, one may observe erroneous changes in intensity due to different probe-sample distances in addition to the desired optical properties of the sample. Constant sample-probe distance is achieved in the present invention by shear force feedback using a crystal tuning fork (not shown). A tapered optical fiber tip 310, as shown in FIGS. 4A–C, is capable of being attached to a tuning fork (not shown) and oscillated at its resonance frequency using an external dither piezo (not shown). As fiber tip 310 approaches the surface of a sample substrate material 320 having for example, a coating 330, the oscillation of the tuning fork is dampened by the tip-sample interaction causing a change in phase and amplitude of the signal out of the tuning fork. Thus, by monitoring the feedback of the phase or amplitude of the crystal tuning fork, the NSOM tip can be held at a constant height above the surface.

A "high-resolution" image produced by the present invention is defined by the size of the aperture of fiber tip 310. Single mode, (i.e., single wavelength) optical fibers are tapered to a sharp point either by chemical etching, such as, for example, HF and toluene, or by using a micro pipette puller (i.e., simultaneously heating the fiber by, for example, a laser and pulling it until it breaks). Fiber tip 310 is then capable of being coated with between about 50 and about 100 nm, more often 50 nm, of Aluminum. This is accomplished by evaporating Aluminum while rotating a fiber such as that used in the present invention at a fixed angle so as not to cover the end of fiber tip 310 to create an aperture having a diameter between about 50 and about 100 nm.

FIG. 4A illustrates a high resolution (i.e., down to about 50 nm) PSIM embodiment of the present invention arranged to detect in a reflection mode. Such an embodiment includes a pump beam source 340, such as a laser beam having a wavelength between about 300 nm and about 1 µm that is optically coupled to fiber tip 310 to achieve a near-field power density of at least about 100 W/cm². Pump beam source 340, is modulated prior to the optical coupling with fiber tip 310, by techniques described herein before, such as a chopper wheel 350, to create a periodic thermal deformation in the form of a bump (not shown) on coating 330 deposited on sample substrate material 320. Fiber tip 310 operates as a near-field probe source to collect scattered radiation due to thermal defect deformation of coating 330, and is directed to a detector 360, such as for example, a megapixel CCD via a beamsplitter 362 after passing through one or more optical elements 370, such as, but not limited to, optical band-pass filters, polarizers, and lenses, etc., to produce photothermal images of one or more predetermined sites using optical, electronic, and mechanical translation techniques as described herein before.

FIG. 4B illustrates another PSIM embodiment of the present invention utilizing fiber tip 310 as a near-field pump source and a far-field probe beam source 312 arranged to detect in an illumination mode. Pump source 340 is again modulated prior to optical coupling with fiber tip 310, by, for example, chopper wheel 350, to create a periodic thermal deformation in the form of a bump (not shown) on coating 330 deposited on sample substrate material 320. In this embodiment, however, far-field probe source 312, i.e., a probe source that images greater than a wavelength from a sample's heat-deformed surface, is capable of being transmitted through, for example, a bottom side of sample substrate material 320, as shown in FIG. 4B, and overlapped at the position where pump beam source 340 illumination, from fiber tip 310, is creating nano-meter sized deformations between 50 and about 125 nm in diameter. Probe beam source 312 is then diffracted and directed, as shown in FIG. 4b, to detector 360, such as a megapixel CCD, after passing through one or more optical elements 370 such as, but not limited to, optical band-pass filters, polarizers, and lenses, etc., to produce photothermal images having a resolution of at least 10 µm of one or more predetermined sites using optical, electronic, and mechanical translation techniques as described herein before.

FIG. 4C illustrates another high-resolution (i.e., down to about 50 nm) PSIM embodiment of the present invention utilizing pump source 340 as a far-field pump source (i.e., the illumination source is not capable of being brought within the near field of the surface) and fiber tip 310 arranged as a near-field probe source to detect in a frustrated total internal reflection mode. In this embodiment, pump source 340, is again capable of being modulated by a chopper wheel 350 and is transmitted through a side of sample, such as, for example, coating 330 that resides on substrate material 320. In this arrangement, pump source 340 is capable of being brought to a focus by coupling optics (not shown) such that pump source 340 can be directed by one or more total internal reflections (TIR) to create a predetermined heat deformation site (not shown). Fiber tip 310 is arranged to collect scattered radiation at such a heat deformed site location and the collected radiation is directed to detector 360, such as a megapixel CCD, after passing through one or more optical elements 370 to produce photothermal images of one or more predetermined sites using optical, electronic, and mechanical translation techniques as described herein before.

Accordingly, embodiments of the present invention are beneficial in providing a rapid, non-destructive optical tool capable of identifying defects and potential laser damage sites in small-aperture (i.e., less than about 5 cm) and large-aperture (i.e., up to about a meter) optics. Moreover, the present invention provides an inspection tool with applications ranging from quality assurance, crack detection, corrosion detection, and bonding properties of various materials.

It should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. An imaging apparatus, comprising:
    a first source of electromagnetic radiation adapted to produce a periodically heat-deformed localized area on a material,
    a second source of electromagnetic radiation adapted to substantially probe the heat-deformed localized area,
    an array detector arranged to collect the second source radiation; and
    an x,y,z translation stage, configured to receive up to about a meter size optic, wherein the x,y,z translation stage coupled with the array detector enables scan times of about 2 seconds per square area of one or more predetermined probed heat-deformed localized areas so as to produce a constructed photothermal image of the optic.

2. The apparatus of claim 1, wherein construction of the photothermal image includes processing the collected radiation in an imaging mode that includes an in-phase and a quadrature optical lock-in of a same frequency modulated second source with respect to the periodicity of the first source.

3. The apparatus of claim 2, wherein a resolution of at least 50 nm is capable of being produced.

4. The apparatus of claim 2, wherein a resolution of at least 10 µm is capable of being produced.

5. The apparatus of claim 1, wherein the first source and the second source are arranged to produce beam diameters between about 50 nm and about 125 nm.

6. The apparatus of claim 1, wherein the first source and the second source are arranged to produce beam diameters between about 2 µm and about 5 mm.

7. The apparatus of claim 1, wherein the first source and the second source include a laser beam having a wavelength range between about 300 nm and about 1 µm.

8. The apparatus of claim 1, wherein the detector includes an array detector selected from a charge coupled device (CCD) array, a liquid nitrogen cooled CCD array, a CCD camera, and an avalanche CCD photodetector.

9. The apparatus of claim 1, wherein the second source is polarized.

10. The apparatus of claim 9, wherein a cross-polarized component of the collected radiation with respect to the second source is analyzed.

11. The apparatus of claim 9, wherein a same polarized component of the collected radiation with respect to the second source is analyzed.

12. The apparatus of claim 1, wherein the apparatus includes a near field scanning optical microscope adapted to operate in a near field probe laser reflection mode.

13. The apparatus of claim 1, wherein the apparatus includes a near field scanning optical microscope adapted to operate in a far field probe laser illumination mode.

14. The apparatus of claim 1, wherein the apparatus includes a near field scanning optical microscope adapted to operate in a frustrated total internal reflection mode.

15. The apparatus of claim 1, wherein the large-aperture material includes an optical sample having a surface area up to about 0.785 $m^2$.

16. An imaging apparatus, comprising:
a first source comprising:
a near field scanning optical microscope, capable of producing a periodically heat-deformed area and additionally capable of substantially probing the periodically heat-deformed area,
a second source capable of probing the periodically heat-deformed area and additionally capable of producing the periodically heat-deformed area,
an array detector arranged to collect a source probe radiation; and
an x,y,z translation stage adapted to investigate one or more predetermined areas on a sample to produce a constructed photothermal image from the collected radiation.

17. The apparatus of claim 16, wherein the apparatus includes a reflection mode arrangement.

18. The apparatus of claim 16, wherein the apparatus includes an illumination mode.

19. The apparatus of claim 16, wherein the apparatus includes a frustrated total internal reflection mode.

20. The apparatus of claim 16, wherein a resolution of at least 50 nm is capable of being produced.

21. The apparatus of claim 16, wherein the sample includes an optic having a surface area up to about 0.785 $m^2$.

22. A method for producing an image, comprising,
optically pumping a localized area on a sample with a first laser beam to produce a periodically heat-deformed area,
probing the heat-deformed area with a second laser beam,
collecting the radiation from the second laser beam with an array detector,
scanning at about 2 seconds per square area a substantially large surface area material of up to about a meter size in dimension to enable investigation of one or more predetermined probed areas on the material, wherein a constructed photothermal image from the one or more predetermined probed areas of the substantially large surface area material is capable of being produced from the collected radiation.

23. The method of claim 22, wherein the first laser beam and the second laser beam are capable of emitting in a wavelength range between about 300 nm and about 1 μm.

24. The method of claim 22, wherein the first laser beam and the second laser beam are arranged to produce beam diameters between about 2 μm and about 5 mm.

25. The method of claim 22, wherein the first source and the second source are arranged to produce beam diameters between about 50 nm and about 125 nm.

26. The method of claim 22, wherein construction of the photothermal image includes processing the collected radiation in an imaging mode that includes an in-phase and a quadrature optical lock-in of a same frequency modulated second source with respect to the periodicity of the first source.

27. The method of claim 22, wherein the detector includes an array detector selected from a two-dimensional array detector, a charge coupled device (CCD) array, a liquid nitrogen cooled CCD array, a CCD camera, and an avalanche CCD photodetector.

28. The method of claim 24, wherein a resolution of at least 10 μm is capable of being produced.

29. The method of claim 24, wherein a resolution of at least 50 nm is capable of being produced.

30. The method of claim 22, wherein optical materials having a surface area up to about 0.785 $m^2$, are capable of being imaged in less than about 8 hours.

* * * * *

UNITED STATES PATENT AND TRADEMARK OFFICE
CERTIFICATE OF CORRECTION

PATENT NO.         : 7,075,058 B2                                        Page 1 of 1
APPLICATION NO.    : 10/402604
DATED              : July 11, 2006
INVENTOR(S)        : Diane Chinn et al.

It is certified that error appears in the above-identified patent and that said Letters Patent is hereby corrected as shown below:

Title Page #7

1. Attorney, Agent, Or firm is missing. It should read:

*Attorney, Agent, or Firm* - Michael C. Staggs; Alan H. Thompson

Signed and Sealed this

Seventh Day of November, 2006

JON W. DUDAS
*Director of the United States Patent and Trademark Office*